United States Patent [19]

Nehring

[11] 4,330,474
[45] May 18, 1982

[54] PROCESS FOR THE MANUFACTURE OF CYCLIC ACETALS OF ALIPHATIC ALDEHYDES

[75] Inventor: Rudolf Nehring, Marl, Fed. Rep. of Germany

[73] Assignee: Chemische Werke Huels, A.G., Marl, Fed. Rep. of Germany

[21] Appl. No.: 42,646

[22] Filed: May 25, 1979

[30] Foreign Application Priority Data

Jun. 26, 1978 [DE] Fed. Rep. of Germany ....... 2827974

[51] Int. Cl.$^3$ .......................................... C07D 319/00
[52] U.S. Cl. ................................................... 549/367
[58] Field of Search ............................. 260/340.6, 340

[56] References Cited

U.S. PATENT DOCUMENTS

| 3,005,799 | 10/1961 | Wagner | 260/340 |
| 3,697,546 | 10/1972 | Asakawa et al. | 260/340 |
| 4,079,064 | 3/1978 | Taylor | 260/340.7 |
| 4,093,752 | 6/1978 | Withycombe et al. | 260/340.6 |

FOREIGN PATENT DOCUMENTS

| 2001070 | 9/1970 | Fed. Rep. of Germany | 260/340.7 |
| 462319 | 3/1937 | United Kingdom | 260/340 |

OTHER PUBLICATIONS

Kirk–Othmer Encyclopedia of Chem. Technology, 2nd Edition, vol. 7, p. 56.
Kirk–Othmer Encyclopedia of Chem. Technology, 2nd Edition, vol. 18, pp. 56, 57, 61, 63, 140, 156 and 157.

*Primary Examiner*—Ethel G. Love
*Attorney, Agent, or Firm*—Millen & White

[57] ABSTRACT

A process for preparing a cyclic acetal from a saturated, aliphatic aldehyde comprises contacting a saturated, aliphatic aldehyde of 2–16 carbon atoms with a silica gel.

5 Claims, No Drawings

PROCESS FOR THE MANUFACTURE OF CYCLIC ACETALS OF ALIPHATIC ALDEHYDES

BACKGROUND OF THE INVENTION

The present invention relates to a process for preparing cyclic acetals of aliphatic, saturated aldehydes.

Cyclic trimers, such as the 2,4,6-trialkyl-(1,3,5)-trioxanes, and tetramers of aliphatic, saturated aldehydes are formed by the action of acid catalysts, such as sulphuric acid, hydrochloric acid or phosphoric acid, or ion exchangers. In general, the aldehydes are passed into an acidified solution while stirring and cooling. After the conclusion of the reaction, the mixture is neutralized with sodium bicarbonate or sodium carbonate. Care must be taken to adjust the equivalent point accurately in order to avoid aldolization reactions in alkaline solutions. The reaction mixture is then distilled in order to remove the salts formed and the water.

Continuous cyclization is carried out by passing aldehydes over acid cation exchangers, but the latter have a limited life. Their properties undergo variation after a short time because of condensation reactions with the reactive aldehydes and because the ion exchangers begin to swell due to the good solubility properties of the aldehydes.

SUMMARY OF THE INVENTION

Accordingly, it is an object of this invention to provide a process for manufacturing cyclic acetals of saturated, aliphatic aldehydes in a simple and economical manner.

Upon further study of the specification and appended claims, further objects and advantages of this invention will become apparent to those skilled in the art.

These objects have been achieved by providing a process for preparing a cyclic acetal from a saturated, aliphatic aldehyde comprising contacting a saturated, aliphatic aldehyde of 2–16 carbon atoms with a silica gel.

DETAILED DISCUSSION

When silica gel is used as the cyclization catalyst, the disadvantages described above do not occur. The reaction mixture need not be neutralized or freed from extraneous substances, and the properties of the silica gel do not undergo variation in long-duration tests. On the contrary, the silica gel can be employed very economically as a fixed bed catalyst by allowing the aldehydes to trickle continuously through a fixed catalyst bed consisting of silica gel beads, and the degree of conversion can be adjusted by means of the residence time. A virtually 100 percent yield is obtained, relative to the conversion. The distillation which should be carried out subsequent to the cyclization serves to remove the unreacted aldehyde; depending on the reactivity of the aldehyde employed, 0 to 5% of residue (polymers with an acetal structure) are isolated in the distillation of the cyclic acetal.

Although the silica gel lacks the strongly acidic properties of the catalysts hitherto used for the manufacture of cyclic acetals of saturated, aliphatic aldehydes, the cyclization takes place with high degrees of conversion. This result is unexpected. A particularly advantageous property of the silica is their great insensitivity to reactive aldehydes, in spite of their high catalyst activity. This permits a long working life and, thus, a great economy of operation in a charge of fixed bed catalyst.

Examples of suitable silica gels include silica gel beads having an $SiO_2$ content of 85 to 98%, preferably 90 to 97%. In general, suitable silica gels have a loss (by weight of water) on drying (110° C.) of <0.1 to 4.0%, preferably 0.1 to 2.0%, a loss on calcination (at 450° C.) of <0.1 to 6.0%, preferably 0.1 to 3.0% and a loss on calcination (at 850° C.) of 1.5 to 10%, preferably 2 to 7%. It is preferable to employ silica gels having a total loss from drying at 110° C. and calcining at 850° C. of at least 2%, especially 2.5 to 10%.

Suitable silica gels include those having the following physical properties:
bead size: 3–6 mm
bulk density: 0.48–0.8 g/cm$^3$
specific pore volume: 0.35–1.0 cm$^3$/g
specific internal surface area: 460–750 m$^2$/g.

Of course, only a catalytically effective amount of the silica gel need be employed. Generally, at any given time, the weight ratio of silicon gel to aldehyde is 1:1000 to 1:0.1.

Suitable saturated, aliphatic aldehydes having 2 to 16 carbon atoms include straight-chain and branched aldehydes, such as, for example, acetaldehyde, propionaldehyde, n-butyraldehyde, isobutyraldehyde, valeraldehyde, caproaldehyde, caprylic aldehyde and lauric aldehyde. They are trimerized in good yields to give the cyclic acetals, such as, for example, the 2,4,6-trialkyl-(1,3,5)-trioxanes.

The manufacture of the cyclic acetals by cyclizing the saturated, aliphatic $C_2$ to $C_{16}$ aldehydes is carried out at temperatures from −20° to +50° C., preferably at −15° to +30° C., and especially at −10° to +20° C. Temperatures above 50° C. should be avoided, since at this temperature scission of the cyclic acetals back into the aldehydes occurs to an increasing extent. Since the reaction, such as, for example, the cyclization of acetaldehyde, is strongly exothermic, it is necessary to control the reaction temperature by cooling.

The temperature should be controlled within the aforementioned limits; preferably, the reaction temperature will be kept constant at a predetermined value selected arbitrarily within these limits with an accuracy of +5° C.

The residence time which is advantageous for high conversion depends on the chain length of the aldehyde employed and increases as the molecular weight rises. Acetaldehyde reacts spontaneously at −10° C.; lauric aldehyde only after some hours at approximately 20° C., i.e., 24–120 hours. In batch operation, reaction times similarly vary from 180 minutes–240 hours.

It is preferred that the reaction be carried out under anhydrous conditions. Generally, at least no more than 0.1–0.4% of water should be present.

The reaction is preferably carried out in the absence of solvents. It can also be carried out in the presence of inert solvents. However, it is advantageous not to add solvents, since the latter must be removed, for example, by distillation, after the conclusion of the acetalization reaction. Atmospheric pressure is suitable and agitation is generally employed in batch operation.

For example, 60 kg of 2,4,6-tripropyl-(1,3,5)-trioxane can be prepared from n-butanal without loss of activity in the catalyst bed after the conclusion of the experiment, by passing through a charge of only 120 g of silica gel beads having the following characteristic values:

|  | Weight percent |
| --- | --- |
| CHEMICAL COMPOSITION: | |
| Content | |
| $SiO_2$ | 91.3 to 96.1 |
| $Na_2O$ | 0.001 to 0.075 |
| $K_2O$ | <0.001 to 0.016 |
| Cl | <0.001 to 0.005 |
| $SO_4$ | 0.01 to 0.024 |
| N | 0.001 to 0.014 |
| C | 0.03 to 0.25 |
| Loss on drying (110° C.) | <0.1 to 0.28% |
| Loss on calcination (at 450° C.) | 0.11 to 2.9% |
| Loss on calcination (at 850° C.) | 2.9 to 5.9% |
| PHYSICAL PROPERTIES: | |
| Bead size | 3 to 6 mm |
| Bulk density | 0.48 to 0.8 g/cm$^3$ |
| Specific pore volume | 0.35 to 1.0 cm$^3$/g |
| Specific internal surface area | 460 to 750 m$^2$/g |

At a throughput of 400 ml/hour × 1 liter of catalyst, a 47% conversion of n-butanal is obtained. Depending on the dimensions of the catalyst bed and the manner in which the reaction is carried out, this rises to 85% on increasing the residence time.

As mentioned, if the cyclic acetals are heated above 50° C. in the presence of silica gel, scission back into the starting products is possible. In the course thereof, the aldehyde is distilled off slowly. The cyclic acetals can thus be employed particularly advantageously as a source of aldehyde for reactions in which side reactions such as, for example, resinification reactions, must be suppressed to a considerable extent. They are also suitable as solvents for fats, oils, waxes and resins and as intermediate products. Trimethyltrioxane is useful as a sedative.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

2,4,6-Trimethyl-(1,3,5)-trioxane 50 g of acetaldehyde are initially placed in a stirred flask equipped with a reflux condenser, a stirrer, a thermometer and a dropping funnel and are cooled to −10° C. with a freezing mixture. Silica gel beads with the following characteristic values:

|  | Percent |
| --- | --- |
| CHEMICAL COMPOSITION: | |
| Content | |
| $SiO_2$ | 96.1 |
| $Na_2O$ | 0.001 |
| $K_2O$ | <0.001 |
| Cl | <0.001 |
| $SO_4$ | 0.024 |
| N | 0.014 |
| C | 0.04 |
| Loss on drying (110° C.) | 0.28% |
| Loss on calcination (400° C.) | 1.6% |
| Loss on calcination (850° C.) | 3.3% |
| PHYSICAL PROPERTIES | |
| Bead size | 3 to 6 mm |
| Bulk density | 0.48 g/cm$^3$ |
| Specific pore volume | 1.0 cm$^3$/g |
| Specific internal surface | 460 m$^2$/g | are added at such a rate that the reaction temperature cannot exceed 0° C. After adding a total of 50 g of the catalyst, 350 g of acetaldehyde are added dropwise over the course of 3 hours. The reaction temperature can vary between −3° and −10° C. The mixture is then allowed to warm up to approximately 15° C., while stirring. The product is decanted off from the silica gel beads and filtered to free it from metaldehyde (tetrameric acetaldehyde). The filtrate is distilled to give 365 g of trimethyltrioxane having a boiling point of 41° to 42° C./30 mm Hg (refractive index = 1.4050).

It is particularly advantageous to place the catalyst together with 100 g of trimethyltrioxane initially in the stirred flask; cool the mixture; and meter acetaldehyde into this mixture. The reaction temperature should be kept constant at −5° C.

EXAMPLE 2

2,4,6-Triethyl-(1,3,5)-trioxane 80 g of the silica gel beads employed in Example 1 are added to 520 g of propionaldehyde at 15° C.; the mixture is stirred for 5 hours at this temperature; the silica gel beads are then filtered off; and the filtrate is distilled: 335 g (65% of theory) distill over at 31° to 33° C./0.4 mm Hg, with a refractive index of 1.4176.

EXAMPLE 3

2,4,6-Tripropyl-(1,3,5)-trioxane

A glass column is filled with 120 g of silica gel beads of the composition described in Example 1 and is charged, at 15° C., with 99.6% pure n-butyraldehyde. The aldehyde is allowed to trickle through the fixed bed at a rate of 0.1 liter/hour and a 47% conversion is obtained. This is increased to 62% if the throughput rate is reduced to 0.05 liter/hour. Distillation gives tripropyltrioxane in a yield of 98%, relative to conversion. Boiling point: 104° to 106° C./16 mm Hg; $n_D^{20} = 1.4265$.

A total of 100 kg of n-butyraldehyde are converted into approximately 63 kg of cyclic acetal with this charge of catalyst without noticeable reduction in the activity of the catalyst on discontinuing the experiment.

If n-butyraldehyde is allowed to stand in an Erlenmeyer flask in the presence of these silica gel beads for 10 days at 15° C., tripropyltrioxane is formed in a yield of 98% (relative to the conversion) at a conversion of 85%.

If n-butyraldehyde is allowed to stand in an Erlenmeyer flask in the presence of the following grades of silica gel beads for 2 days at 20° C., the following yields are obtained:

|  | Example | | |
|---|---|---|---|
|  | 3.1 | 3.2 | 3.3 |
| CHEMICAL PROPERTIES: | | | |
| Loss on drying, 120° C. | <0.1% | <0.1% | <0.1% |
| Loss on calcination, 450° C. | 0.55% | 2.89% | 0.11% |
| Loss on calcination, 850° C. | 2.9% | 4.87% | 5.82% |
| Content | | Percent | |
| $SiO_2$ | 93.8 | 92.3 | 91.3 |
| $Na_2O$ | 0.0635 | 0.0594 | 0.0740 |
| $K_2O$ | 0.0160 | 0.0145 | 0.0120 |
| Cl | 0.0030 | 0.0040 | 0.0030 |
| $SO_4$ | 0.013 | 0.02 | 0.01 |
| N | 0.001 | 0.003 | 0.001 |
| C | 0.07–0.08 | 0.22–0.25 | 0.03 |
| PHYSICAL PROPERTIES: | | | |
| Bead size | approx. 3.5mm | approx. 3.5mm | approx. 3.5mm |
| Bulk density | 0.7 g/cm³ | 0.7 g/cm³ | 0.8 g/cm³ |
| Specific pore volume | 0.4 cm³/g | 0.47 cm³/g | 0.35 cm³/g |
| Specific internal surface | 650 m²/g | 750 m²/g | 750 m²/g |
| Yield | 75% | 76% | 79% |

Tripropyltrioxane can be split in a simple manner by heating to 70°–100° C. in the presence of the silica gel catalyst, from tripropyltrioxane to which silica gel beads have been added (in a ratio of 1:10), it is possible to distil off approximately 95% of the n-butyraldehyde, which is produced in a purity of over 99.9% after the scission reaction.

EXAMPLE 4

2,4,6-Triisopropyl-(1,3,5)-trioxane 1,060 g of i-butyraldehyde are stirred with 100 g of silica gel beads of the characteristic values described in Example 1 for 15 hours at 15° C.; the catalyst beads are removed and the mash of crystals formed is filtered off and washed with i-butyraldehyde. After drying in vacuo, 710 g (67% of theory) of the crystalline trioxane with a melting point of 58° to 59° C. are obtained. A further 220 g of trioxane can be isolated from the mother liquor by filtration, after concentrating and cooling the solution.

EXAMPLE 5

2,4,6-Tributyl-(1,3,5)-trioxane 100 g of n-valeraldehyde are mixed at 15° C. with 20 g of the silica gel beads employed in Example 1 and the mixture is stirred for 48 hours at 15° C. After the catalyst has been removed, the residue is distilled. This gives 73 g (73% of theory) of trioxane having a boiling point of 105° to 109° C./0.4 mm Hg and a refractive index of 1.4338.

EXAMPLE 6

2,4,6-Tripentyl-(1,3,5)-trioxane 560 g of caproaldehyde are stirred at 15° C. with 50 g of the silica gel beads employed in Example 1 for 3 days. After removing the catalyst, distillation gives 205 g (37% of theory) of 2,4,6-tripentyl-(1,3,5)-trioxane having the following boiling point and refractive index: 118° to 120° C./0.2 mm Hg; $n_D^{20} = 1.4415$.

EXAMPLE 7

2,4,6-Triheptyl-(1,3,5)-trioxane 100 g of the silica gel beads employed in Example 1 are added to 700 g of caprylic aldehyde and the mixture is stirred at 15° C. for 4 days. The product solidifies to give a mash of crystals, which is dissolved in acetone. After filtration, the filtrate is cooled to 0° C. and filtered. This gives 235 g of trioxane which crystallizes in fine needles with a melting point of 29° to 30° C. An additional 145 g are obtained from the mother liquor by concentrating the solution.

EXAMPLE 8

2,4,6-Triundecyl-(1,3,5)-trioxane 25 g of silica gel beads are added to 195 g of n-dodecanal and the mixture is stirred at 15° to 20° C. for 5 days. The resulting mash of crystals is dissolved in acetone at 35° to 40° C. and is filtered; the filtrate is cooled to 0° C. and the mash of crystals precipitated is filtered off and dried in vacuo: 109 g of triundecyltrioxane with a melting point of 39.5° to 40.5° C. are obtained. Additional trioxane is obtained by concentrating and cooling the mother liquor and filtering off the precipitate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 2,4,6-trialkyl-(1,3,5)-trioxane by cyclizing under anhydrous conditions a saturated, aliphatic aldehyde, consisting essentially of contacting a saturated, aliphatic aldehyde of 2–16 carbon atoms with a silica gel of 90% to 97% $SiO_2$.

2. The process of claim 1 wherein the aldehyde is trickled continuously through a fixed catalyst bed of silica gel beads.

3. The process of claim 1 wherein the silica gel has a total loss on drying at 110° C. and calcining at 850° C. of 2–10%.

4. The process of claim 1 wherein the reaction is carried out at a temperature of −20° to +50° C.

5. The process of claim 3 wherein the reaction is carried out at a temperature of −20° to +50° C. and under anhydrous conditions.

* * * * *